United States Patent
Schwarz

(10) Patent No.: US 7,105,175 B2
(45) Date of Patent: *Sep. 12, 2006

(54) IMPLANTABLE OR INSERTABLE MEDICAL DEVICES FOR CONTROLLED DELIVERY OF A THERAPEUTIC AGENT

(75) Inventor: Marlene C. Schwarz, Auburndale, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 331 days.

This patent is subject to a terminal disclaimer.

(21) Appl. No.: 10/175,334

(22) Filed: Jun. 19, 2002

(65) Prior Publication Data

US 2003/0235602 A1   Dec. 25, 2003

(51) Int. Cl.
*A61F 13/00* (2006.01)
*A61F 2/00* (2006.01)

(52) U.S. Cl. .................. 424/422; 424/423; 424/424

(58) Field of Classification Search ............... 424/422, 424/423, 436
See application file for complete search history.

(56) References Cited

U.S. PATENT DOCUMENTS

| | | | |
|---|---|---|---|
| 4,946,899 A | 8/1990 | Kennedy et al. | 525/244 |
| 5,019,096 A * | 5/1991 | Fox, Jr. et al. | 600/36 |
| 5,258,020 A | 11/1993 | Froix | 623/1 |
| 5,304,121 A | 4/1994 | Sahatjian | 604/53 |
| 5,607,463 A * | 3/1997 | Schwartz et al. | 623/1.44 |
| 5,616,608 A | 4/1997 | Kinsella et al. | 514/449 |
| 5,716,981 A | 2/1998 | Hunter et al. | 514/449 |
| 5,733,925 A | 3/1998 | Kunz et al. | 514/449 |
| 5,741,331 A | 4/1998 | Pinchuk | 623/11 |
| 5,756,145 A * | 5/1998 | Darouiche | 427/2.24 |
| 5,824,049 A * | 10/1998 | Ragheb et al. | 623/1.44 |
| 5,837,008 A * | 11/1998 | Berg et al. | 128/898 |
| 5,879,697 A | 3/1999 | Ding et al. | 424/422 |
| 5,954,706 A | 9/1999 | Sahatjian | 604/509 |
| 6,054,504 A * | 4/2000 | Dalla Riva Toma | 523/122 |
| 6,099,562 A | 8/2000 | Ding et al. | 623/1.46 |
| 6,280,411 B1 | 8/2001 | Lennox | 604/103.05 |

(Continued)

FOREIGN PATENT DOCUMENTS

EP    0 328 421 A2 *   8/1989

(Continued)

OTHER PUBLICATIONS

Perez-Camacho "Preparation of Hydroxyl-Functionalized SEBS fro In Situ GRaft Reaction Compatibilizing Agents", Journal of Applied Polymer Science, 64(13):2519-2528 (1997).*

*Primary Examiner*—S. Tran
(74) *Attorney, Agent, or Firm*—Mayer & Williams PC; David B. Bonham, Esq.

(57) ABSTRACT

The present invention is directed to novel implantable or insertable medical devices that provide controlled release of a therapeutic agent. According to an embodiment of the present invention, a therapeutic-agent-releasing medical device is provided, which comprises: (a) an implantable or insertable medical device; (b) a release layer disposed over at least a portion of the implantable or insertable medical device; and (c) a therapeutic agent. The release layer comprises a styrene copolymer and at least one additional polymer. The release layer regulates the rate of release of the therapeutic agent from the medical device upon implantation or insertion of the device into a patient. The present invention is also directed to methods of forming the above implantable or insertable medical devices, methods of administering a therapeutic agent to a patient using such devices, and methods of modulating the release of therapeutic agent from such devices.

39 Claims, 6 Drawing Sheets

U.S. PATENT DOCUMENTS

| | | |
|---|---|---|
| 6,306,166 B1 * | 10/2001 | Barry et al. ................ 623/1.46 |
| 6,306,419 B1 * | 10/2001 | Vachon et al. .............. 424/422 |
| 6,335,029 B1 | 1/2002 | Kamath et al. ............. 424/423 |
| 6,630,215 B1 * | 10/2003 | Oda et al. ................... 428/35.7 |
| 2002/0107330 A1 | 8/2002 | Pinchuk et al. ............. 525/242 |
| 2003/0074049 A1 * | 4/2003 | Hoganson et al. ......... 623/1.13 |
| 2003/0139800 A1 * | 7/2003 | Campbell ................... 623/1.15 |
| 2003/0143315 A1 * | 7/2003 | Pui et al. ...................... 427/2.1 |
| 2004/0142015 A1 * | 7/2004 | Hossainy et al. ........... 424/423 |

FOREIGN PATENT DOCUMENTS

| | | | |
|---|---|---|---|
| EP | 0328421 A2 | 8/1989 | |
| JP | 59232940 A * | 12/1984 | |
| WO | WO 84/01721 | 5/1984 | |
| WO | WO 86/02006 | 4/1986 | |
| WO | WO 86/02006 A1 * | 4/1986 | |
| WO | WO 98/56312 A1 * | 12/1998 | |
| WO | WO 00/41647 | 7/2000 | |
| WO | WO 00/62830 | 10/2000 | |
| WO | WO 00/62830 A2 * | 10/2000 | |
| WO | WO 02/47731 A2 | 6/2002 | |
| WO | WO 03/035135 | 5/2003 | |

* cited by examiner

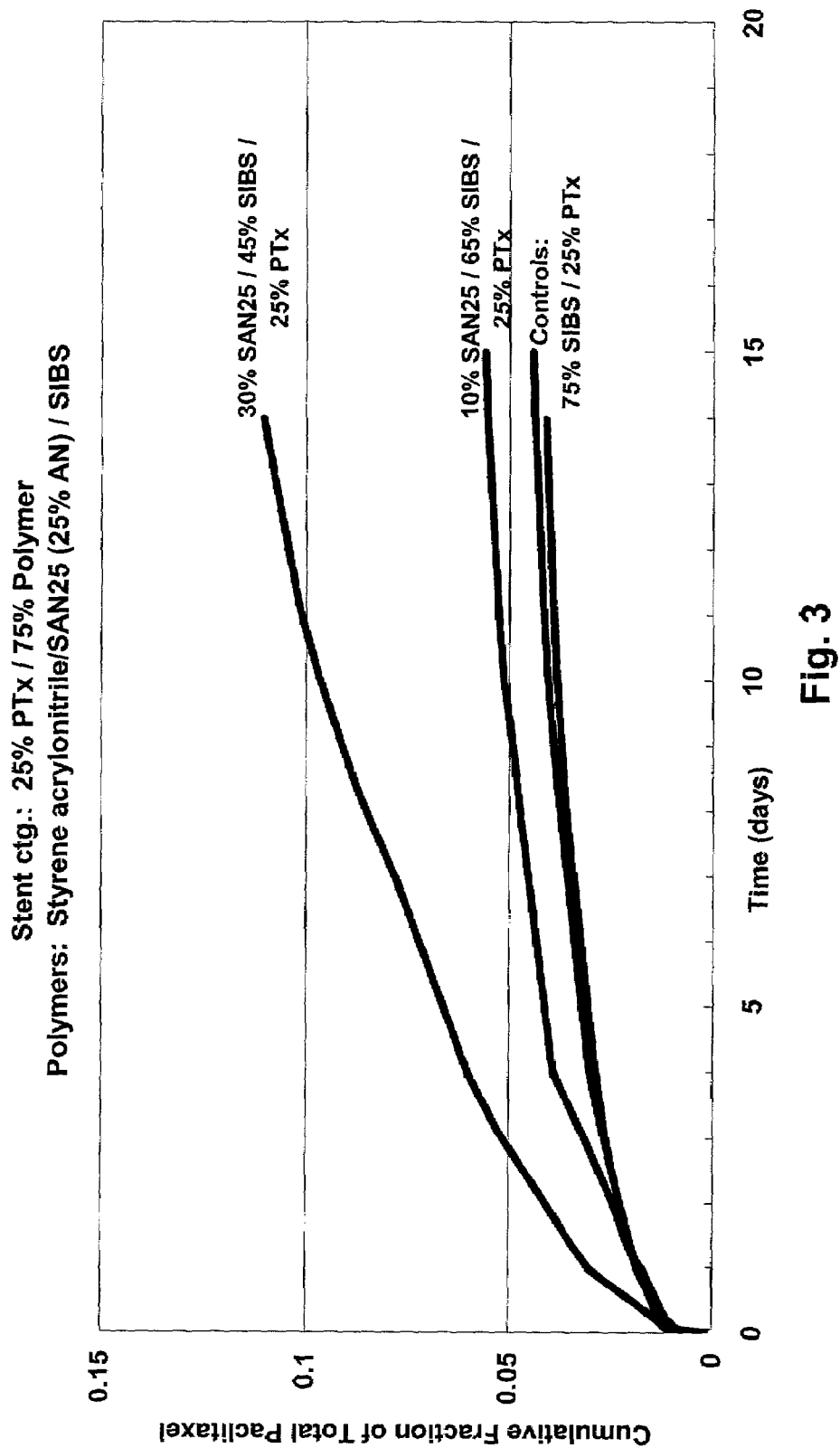

IMPLANTABLE OR INSERTABLE MEDICAL DEVICES FOR CONTROLLED DELIVERY OF A THERAPEUTIC AGENT

FIELD OF THE INVENTION

The present invention relates to implantable or insertable medical devices for controlled delivery of one or more therapeutic agents.

BACKGROUND OF THE INVENTION

Numerous medical devices have been developed for the delivery of therapeutic agents to the body.

In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. As a result, there is a continuing need for polymeric layers, including polymeric barrier layers and carrier layers, that are able to provide a broad range of therapeutic agent release rates.

SUMMARY OF THE INVENTION

The present invention is directed to novel implantable or insertable medical devices, which provide for release of a therapeutic agent. According to a first aspect of the present invention, a therapeutic-agent-releasing medical device is provided, which comprises: (a) an implantable or insertable medical device; (b) a release layer disposed over at least a portion of the implantable or insertable medical device; and (c) a therapeutic agent. The release layer comprises a styrene copolymer and an additional polymer. The release layer regulates the rate of release of the therapeutic agent from the medical device upon implantation or insertion of the device into a patient. Alternating and random styrene copolymers are preferred.

In some embodiments, the release layer is a carrier layer that comprises the therapeutic agent. In other embodiments, the release layer is a barrier layer disposed over a therapeutic-agent-containing region, which comprises the therapeutic agent.

Preferred medical devices include catheters, guide wires, balloons, filters, stents, stent grafts, vascular grafts, vascular patches, shunts, and intraluminal paving systems. The device can be adapted, for example, for implantation or insertion into the coronary vasculature, peripheral vascular system, esophagus, trachea, colon, biliary tract, urinary tract, prostate or brain.

Beneficial therapeutic agents for the practice of the present invention include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

Preferred styrene copolymers include copolymers comprising (a) a styrene monomer and (b) a monomer comprising a carbon-carbon double bond. Monomers comprising a carbon-carbon double bond include alkylene monomers (e.g., ethylene, propylene, butadiene, butylenes, isobutylene and isoprene), vinyl monomers (e.g., vinyl ethers, vinyl acetates, vinyl aliphatics, halogenated vinyl compounds, vinyl pyrrolidone, acrylonitrile, vinyl alcohols, and vinyl acrylamides), acrylate monomers or derivatives of the same (e.g., methyl acrylate, methyl methacrylate, acrylic acid, methacrylic acid, hydroxyethyl acrylate, hydroxyethyl methacrylate, glyceryl acrylate, glyceryl methacrylate, acrylamide, methacrylamide and ethacrylamide), and maleic anhydride monomers or derivatives of the same (e.g., maleic anhydride, maleic anhydride in a free acid form, maleic anhydride in a salt form, or maleic anhydride in a partial ester form). Specific styrene copolymers for the practice of the present invention include copolymers of styrene and maleic anhydride and copolymers of styrene and acrylonitrile. In some embodiments, the additional polymer is blended with the styrene copolymer in the release layer. In others, the additional polymer is crosslinked with the styrene copolymer in the release layer. Specific examples of additional polymers for the practice of the present invention include elastomers such as the following: (1) copolymers containing (a) one or more blocks of polyisobutylene and (b) one or more blocks of polystyrene or poly-alpha-methylstyrene, (2) copolymers containing (a) one or more blocks of polystyrene or poly-alpha-methylstyrene and (b) one or more polymer blocks of ethylene and butylene, and (3) poly(butyl methacrylates).

According to another aspect of the present invention, a method of making a therapeutic-agent-releasing medical device is provided. The method comprises: (a) providing a solution comprising one or more solvents, a styrene copolymer and an additional polymer; (b) applying the solution to a surface of an implantable or insertable medical device; and (c) removing the solvents from the solution to form a release layer. Solvent spraying is a preferred technique for applying the above solution.

In some embodiments, for example, where a carrier layer is being formed, the solution further comprises the therapeutic agent. In other embodiments, for example, where a barrier layer is being formed, the solution is applied over a therapeutic-agent-containing region that comprises the therapeutic agent.

According to another aspect of the present invention, a method of modulating a rate of release of a therapeutic agent from a release layer is provided. The release layer is disposed over at least a portion of an implantable or insertable medical device and comprises a styrene copolymer and an additional polymer. Release is modulated by changing the composition of the release layer. In some embodiments, the release rate can be modulated by changing the amount of the styrene copolymer relative to the amount of the additional polymer. For example, the rate of release of the therapeutic agent can be increased in certain embodiments by increasing the amount of the styrene copolymer relative to the amount of the additional polymer, while the rate of release can be decreased by decreasing the amount of the styrene copolymer relative to the amount of the additional polymer.

In other embodiments, the release rate is modulated by changing the molecular weight of the styrene copolymer. In still other embodiments, the release rate is modulated by changing the amount of the styrene monomer relative to the total amount of monomer within the styrene copolymer.

One advantage of the present invention is that implantable or insertable medical devices are provided, which provide for controlled release of a therapeutic agent.

Another advantage of the present invention is that implantable or insertable medical devices are provided, which are able to provide therapeutic agent release over a wide variety of time frames.

Another advantage of the present invention is that effective strategies are provided for controlling the release profile of a therapeutic agent from an implantable or insertable medical device.

These and other embodiments and advantages of the present invention will become immediately apparent to those of ordinary skill in the art upon review of the Detailed Description and Claims to follow.

BRIEF DESCRIPTION OF THE DRAWINGS

FIG. 3 illustrates cumulative release of paclitaxel as a function of time for carrier layers containing paclitaxel and (a) a polystyrene-polyisobutylene-polystyrene block copolymer, and (b) a polystyrene-polyisobutylene-polystyrene block copolymer blended with various amounts of styrene-co-acrylonitrile copolymer, in accordance with an embodiment of the present invention.

DETAILED DESCRIPTION OF THE INVENTION

Figure 1:
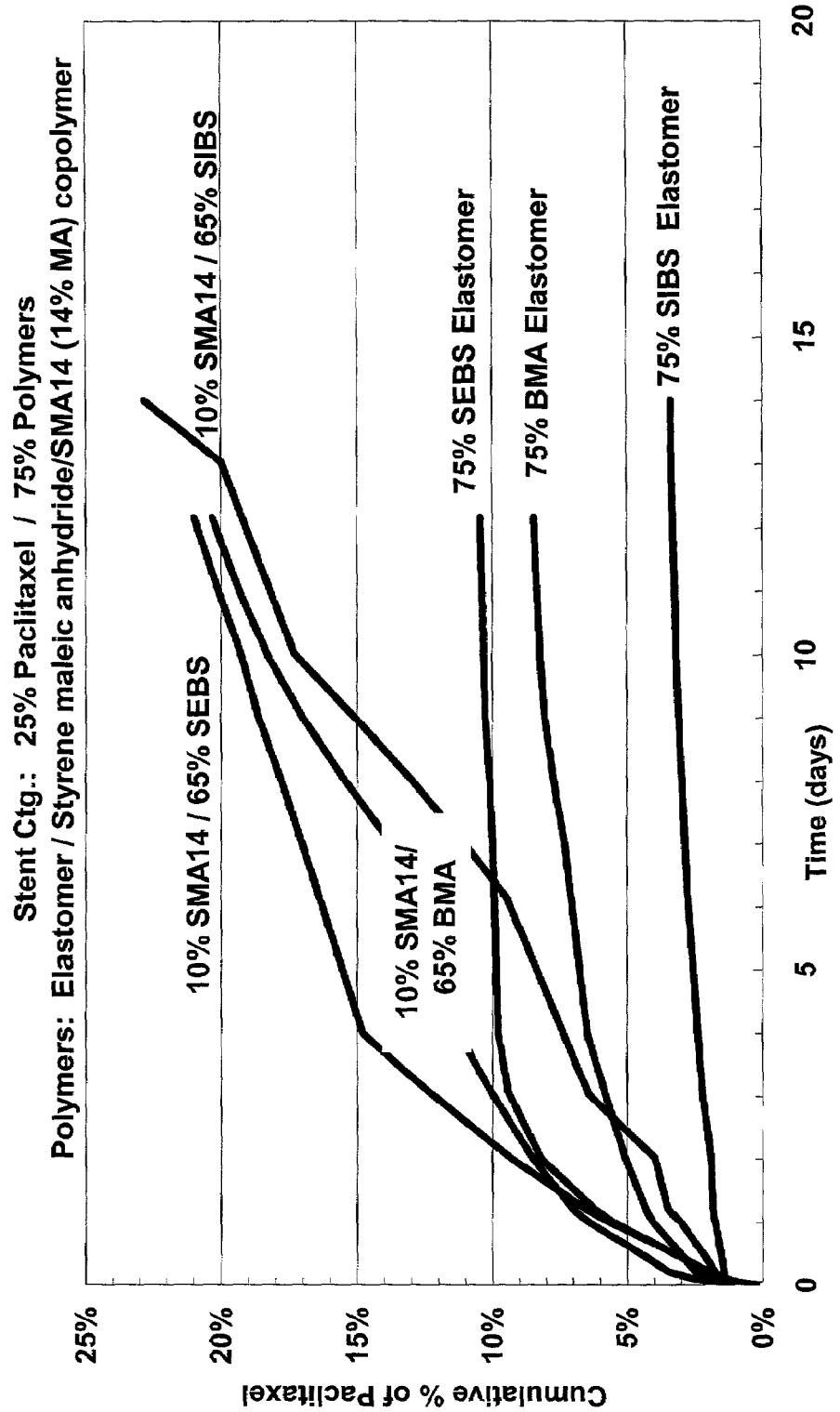
FIG. 1 illustrates cumulative release of paclitaxel as a function of time for carrier layers containing paclitaxel and (a) poly(butyl methacrylate) homopolymer, (b) polystyrene-polyisobutylene-polystyrene block copolymer, (c) polystyrene-b-poly(ethylene-r-butylene)-b-polystyrene block copolymer, (d) poly(butyl methacrylate) homopolymer blended with a random copolymer of styrene and maleic anhydride, (e) polystyrene-polyisobutylene-polystyrene block copolymer blended with a random copolymer of styrene and maleic anhydride and (f) polystyrene-b-poly(ethylene-r-butylene)-b-polystyrene block copolymer blended with a random copolymer of styrene and maleic anhydride.

The present invention relates to the use of styrene copolymers in release layers that control the release of therapeutic agent from an implantable or insertable medical device.

By "release layer" is meant a layer that regulates the rate of release of a therapeutic agent. Two preferred release layers for use in accordance with the present invention are carrier layers and barrier layers.

By "carrier layer" is meant a layer which contains a therapeutic agent and from which the therapeutic agent is released.

By "barrier layer" is meant a layer which is disposed between a source of therapeutic agent and a site of intended release and which impedes the rate at which the therapeutic agent is released.

According to one aspect of the present invention, a medical device is provided which comprises an outer carrier layer disposed over at least a portion of an implantable or insertable medical device. The outer carrier layer comprises a styrene copolymer, an additional polymer and a therapeutic agent. Upon implantation or insertion of the device, the therapeutic agent is released from the carrier layer in a controlled fashion.

According to another aspect of the present invention, an implantable or insertable medical device is provided, which comprises (a) a therapeutic-agent-containing region and (b) a barrier layer comprising a styrene copolymer and an additional polymer over the therapeutic-agent-containing region. Because the barrier layer is disposed over the therapeutic-agent-containing region, the barrier layer acts to control release of the therapeutic agent from the medical device after implantation or insertion of the same.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including GDC—Guglilmi detachable coils—and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent, which delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o)agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs(6-mercaptopurine), pyrimidine analogs (e.g., cytarabine and 5-fluorouracil) and methotrexate , nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

The present invention utilizes release layers comprising a styrene copolymer and an additional polymer.

A "styrene copolymer" is a polymer formed from two or more dissimilar monomers, at least one of which is styrene, or a styrene derivative (e.g., alpha-methyl styrene, ring-alkylated styrenes or ring-halogenated styrenes, or other substituted styrenes where one or more substituents are present on the aromatic ring). Such copolymers may be, for example, random copolymers, alternating copolymers, block copolymers or graft copolymers, and may be, for example, linear, star-shaped, or branched in form. Copolymers comprising random polymer chains formed from two or more dissimilar monomers, at least one of which is styrene or a styrene derivative (referred to herein as "random styrene copolymers") and copolymers comprising alternating polymer chains formed from two or more dissimilar monomers, at least one of which is styrene or a styrene derivative (referred to herein as "alternating styrene copolymers") are preferred.

Examples of styrene copolymers for the practice of the present invention include copolymers of: (1) a monomer of styrene or a styrene derivative with (2) at least one additional monomer, preferably selected from unsaturated monomers such as: (a) alkylene monomers, such as ethylene, propylene, butadiene, butylenes (e.g., butylene, isobutylene), and isoprene; (b) halogenated alkylene monomers (e.g., tetrafluoroethylene and chloroethylene); (c) vinyl monomers and derivatives, such as, methyl vinyl ether, vinyl acetate, vinyl ethylene (butadiene), vinyl chloride, vinyl pyrrolidone, vinyl cyanide (acrylonitrile), and vinyl alcohol; (d) acrylic acid monomers and derivatives, such as methyl acrylate, methyl methacrylate, acrylic acid, methacrylic acid, hydroxyethyl acrylate, hydroxyethyl methacrylate, glyceryl acrylate, glyceryl methacrylate, acrylamide, methacrylamide and ethacrylamide; and (e) maleic anhydride monomers and derivatives, including maleic anhydride, maleic anhydride in a free acid form, maleic anhydride in a salt form, and maleic anhydride in a partial ester form.

Specific examples of styrene copolymers include acrylonitrile-butadiene-styrene copolymers, acrylonitrile-chlorinated polyethylene-styrene copolymers, acrylonitrile-styrene-acrylate copolymers, acrylonitrile-ethylene-propylene-styrene copolymers, ethylene-styrene copolymers, methyl methacrylate-butadiene-styrene copolymers, methyl methacrylate-acrylonitrile-butadiene-styrene copolymers, olefin modified styrene acrylonitrile copolymers, butadiene-styrene copolymers, styrene-isoprene copolymers, styrene-acrylonitrile copolymers, styrene-ethylene-butylene copolymers, styrene-maleic anhydride copolymers, and styrene-methyl methacrylate copolymers.

In forming the release layers of the present invention, the styrene copolymers are blended or crosslinked with one or more additional polymers. The additional polymers may be, for example, homopolymers or copolymers, crosslinked or uncrosslinked, linear or branched, natural or synthetic, thermoplastic or thermosetting.

Additional polymers include the following: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, 1- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Some exemplary additional polymers for use in combination with the present invention are block copolymers comprising at least two polymeric blocks A and B. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule.

One specifically preferred group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block with the triblock therefore denoted as BAB). Where n=3 or more, these structures are commonly referred to as star-shaped block copolymers.

Other examples of additional polymers include branched block copolymers such as dendritic block copolymers (e.g., arborescent block copolymers), wherein at least one of the A and B blocks is branched, and preferably wherein the A blocks are branched and capped by the B blocks.

The A blocks are preferably soft elastomeric components which are based upon one or more polyolefins or other polymer with a glass transition temperature at or below room temperature. For example, the A blocks can be polyolefinic blocks having alternating quaternary and secondary carbons of the general formulation: -(CRR'-CH$_2$)$_n$-, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Preferred polyolefinic blocks include blocks of isobutylene,

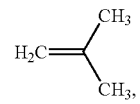

(i.e., polymers where R and R' are the same and are methyl groups). Other examples of A blocks include silicone rubber blocks and acrylate rubber blocks.

The B blocks are preferably hard thermoplastic blocks with glass transition temperatures significantly higher than the elastomeric A block that, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene

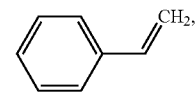

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) made from monomers of methylmethacrylate, ethylmethacrylate hydroxyethyl methacrylate or mixtures of the same.

More preferred are additional polymers that are elastomeric. As defined herein, an "elastomeric" polymer is a polymer that can be stretched to at least 1.5 times its original length at room temperature and, upon release of the stretching stress, will return with force to its approximate original length.

In some particularly preferred embodiments of the present invention, a styrene copolymer is combined with one or more of the following elastomers: (a) a copolymer of polyisobutylene with polystyrene or poly-alpha-methylstyrene, more preferably polystyrene-polyisobutylene-polystyrene triblock copolymers which, along with other polymers appropriate for the practice of the present invention, are described, for example, in U.S. Pat. Nos. 5,741,331, 4,946, 899 and U.S. Ser. No. 09/734,639, each of which is hereby incorporated by reference in its entirety; (b) a copolymer containing one or more blocks of polystyrene and one or more random polymer blocks of ethylene and butylene, for example, a polystyrene-polyethylene/butylene-polystyrene (SEBS) block copolymer, available as Kraton™ G series polymers available from Kraton Polymers; (c) a homopolymer of n-butyl methacrylate (BMA); and (d) arborescent polyisobutylene-polystyrene block copolymers such as those described in Kwon et al., "Arborescent Polyisobutylene-Polystyrene Block Copolymers-a New Class of Thermoplastic Elastomers," *Polymer Preprints*, 2002, 43(1), 266, which is hereby incorporated by reference in its entirety.

The release characteristics associated with the release layers of the present invention can be varied in a number of ways, including the following: (a) varying the type of styrene copolymer(s) used within the release layer, (b) varying the molecular weight of the styrene copolymer(s) used within the release layer, (c) varying the relative amount of styrene monomer in the copolymer, relative to the other monomers, and (d) varying the type, molecular weight and/or relative amount of the additional polymer. Several of these effects are demonstrated in the Examples below.

Medical devices having a sustained release profile are preferred in many cases. By "sustained release profile" is meant a release profile in which less than 25% of the total release from the medical device that occurs over the course of implantation/insertion in the body occurs within the first 1–3 days of administration. Conversely, this means that more than 75% of the total release from the medical device will occur after the device has been implanted/inserted for 1–3 days.

In general, the release layers of the present invention are formed using any number of known techniques. Solvent-based techniques, in which the styrene copolymer and the additional polymer are dissolved or dispersed in a solvent prior to layer formation, are preferred.

Where solvent-based techniques are used, the solvent system that is selected will contain one or more solvent species. The solvent system preferably is a good solvent for the polymers and, where included, for the therapeutic agent as well. The particular solvent species that make up the solvent system may also be selected based on other characteristics including drying rate and surface tension.

Solvent species that can be used in connection with the present invention include any combination of one or more of the following: (a) water, (b) alkanes such as ethane, hexane, octane, cyclohexane, heptane, isohexane, butane, pentane, isopentane, 2,2,4-trimethlypentane, nonane, decane, dodecane, hexadecane, eicosane, methylcyclohexane, cis-decahydronaphthalene and trans-decahydronaphthalene, (c) aromatic species such as benzene, toluene, xylene(s), naphthalene, styrene, ethylbenzene, 1-methylnaphthalene, 1,3,5-trimethylbenzene, tetrahydronaphthalene, diphenyl and 1,4-diethylbenzene, (d) halohydrocarbons including (i) chlorohyhdrocarbons such as chloroform, methyl chloride, dichloromethane, 1,1-dichloroethylene, ethylene dichloride, ethylidene chloride, propyl chloride, cyclohexyl chloride, 1,1,1-trichloroethane, perchloroethylene, trichloroethylene, butyl chloride, carbon tetrachloride, tetrachloroethylene, chlorobenzene, o-dichlorobenzene, benzyl chloride, trichlorobiphenyl, methylcyclohexane, 1,1,2,2-tetrachloroethane (ii) fluorinated halogenated species such as chlorodiflouoromethane, dichlorofluoromethane, dichlorodifluoromethane, trichlorofluoromethane, 1,2-dichlorotetrafluoroethane, 1,1,2-trichlorotrifluoroethane, perfluor(methylcyclohexane), perfluor(dimethylcyclohexane) and (iii) other halohydrocarbons such as ethyl bromide, ethylidene bromide, ethylene dibromide, tribromomethane, bromotrifluoromethane, 1,1,2,2-tetrabromoethane, bromobenzene, bromochloromethane, 1-bromonaphthalene, methyl iodide, methylene diiodide (e) acid aldehydes/anhydrides such as acetaldehyde, furfural, butyraldehyde, benzaldehyde, acetyl chloride, succinic anhydride and acetic anhydride, (f) alcohols including (i) phenols such as phenol, 1,3-benzenediol, m-cresol, o-methoxyphenol, methyl salicylate and nonylphenol, (ii) polyhydric alcohols such as ethylene glycol, glycerol, propylene glycol, 1,3-butanediol, diethylene glycol, triethylene glycol, hexylene glycol and dipropylene glycol, and (iii) other alcohols such as methanol, ethanol, ethylene cyanohydrin, allyl alcohol, 1-propanol, 2-propanol, 3-chloropropanol, furfuryl alcohol, 1-butanol, 2-butanol, benzyl alcohol, isobutanol, cyclohexanol, 1-pentanol, 2-ethyl-1-butanol, diacetone alcohol, 1,3-dimethyl-1-butanol, ethyl lactate, butyl lactate, ethylene glycol monomethyl ether, ethylene glycol monoethyl ether, diethylene glycol monomethyl ether, diethylene glycol monoethyl ether, ethylene glycol monobutyl ether, 2-ethyl-1-hexanol, 1-octanol, 2-octanol, diethylene glycol monobutyl ether, 1-decanol, 1-tridecyl alcohol, nonyl-phenoxy ethanol, oleyl alcohol, triethylene glycol mono-oleyl ether, (g) ethers such as, epichlorohydrin, furan, 1,4-dioxane, dimethoxymethane, diethyl ether, bis-(2-chloroethyl) ether, anisole, di-(2-methoxyethyl) ether, dibenzyl ether, di-(2-chloroisopropyl) ether, bis-(m-phenoxyphenol) ether, dimethyl ether and tetrahydrofuran, (h) ketones, such as acetone, cylohexanone, isophorone, diethyl ketone, mesityl oxide, acetophenone, methyl ethyl ketone, methyl isoamyl ketone, methyl isobutyl ketone, and methyl propyl ketone, (i) acids such as formic acid, acetic acid, benzoic acid, butyric acid, octanoic acid, oleic acid, stearic acid, (j) esters/acetates such as ethylene carbonate, butyrolactone, propylene-1,2-carbonate, ethyl chloroformate, ethyl acetate, trimethyl phosphate, diethyl carbonate, diethyl sulfate, ethyl formate, methyl acetate, n-butyl acetate, isobutyl acetate, t-butyl acetate, 2-ethoxyethyl acetate, isoamyl acetate, dimethyl phthalate, ethyl cinnamate, triethyl phosphate, diethyl phosphate, butyl benzyl phthalate, dibutyl phthalate, diethyl phthalate, tricrysyl phosphate, tributyl phosphate, dibutyl sebacate, methyl oleate, dioctyl phthalate, dibutyl stearate isopropyl acetate, isobutyl isobutyrate, n-propyl acetate and n-butyl propionate, (k) nitrogen compounds such as acetonitrile, acrylonitrile, propionitrile, butyronitrile, nitromethane, nitroethane, 2-nitropropane, nitrobenzene, ethanolamine, ethylenediamine, 1,1-dimethylhydrazine, 2-pyrrolidone, pyridine, propylamine, morpholine, analine, n-methyl-2-pyrrolidone, butylamine, diethylamine, cyclohexylamine, quinoline, dipropylamine, formamide, n,n-dimethylformamide, n,n-dimethylacetamide, tetramethylurea, hexamethyl phosphoramide, diethylenetriamine, triethylamine and triethanolamine, and (l) sulfur compounds such as carbon disulfide, dimethylsulfoxide, ethanethiol, dimethyl sulfone and diethyl sulfide.

Preferred solvent-based techniques include, but are not limited to, solvent casting techniques, spin coating techniques, web coating techniques, solvent spraying techniques, dipping techniques, techniques involving coating via mechanical suspension, including air suspension, ink jet techniques, electrostatic techniques, and combinations of these processes. Typically, a solution containing solvent and polymers (and, in some cases, a therapeutic agent) is applied to a substrate to form a release layer (e.g., a carrier layer or barrier layer). The substrate is typically all or a portion of an implantable or insertable medical device, to which the release layer is applied.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

In the case of a carrier layer, for example, a therapeutic agent can be included in the above-described polymer solution if desired, and hence co-established with the carrier layer. In other embodiments, on the other hand, the therapeutic agent can be dissolved or dispersed within a solvent, and the resulting solution contacted with a previously formed layer, for example, using one or more of the solvent based application techniques described above (e.g., dipping, spraying, etc.).

Barrier layers, on the other hand, are formed over a therapeutic-agent-containing region. In some embodiments, however, the therapeutic-agent-containing region comprises one or more polymers, which can be selected, for example, from the polymers listed above. As such, the therapeutic-agent-containing region can also be established using solvent-based techniques (e.g., dipping, spraying, etc.) such as those discussed above. In other embodiments, the therapeutic-agent-containing region beneath the barrier layer is established without an associated polymer. For example, the therapeutic agent can simply be dissolved or dispersed in a liquid, and the resulting solution/dispersion contacted with a substrate, for instance, using one or more of the above-described application techniques.

Where the release layer is formed using a solvent based technique, it is preferably dried after application to remove the solvents. The release layer typically further conforms to the underlying surface during the drying process.

The invention is further described with reference to the following non-limiting Examples.

EXAMPLE 1

A solution is provided that contains 25 weight % tetrahydrofuran (THF), 74 wt % toluene, 0.25 wt % paclitaxel and 0.75 wt % of a polymer composition or blend.

One control solution is prepared by mixing 0.75 wt % of the block copolymer polystyrene-polyisobutylene-polystyrene block copolymer (SIBS) with the solvents and paclitaxel. The SIBS copolymer is synthesized using known techniques such as those described in U.S. Pat. Nos. 5,741,331, 4,946,899 and U.S. Ser. No. 09/734,639.

A first corresponding test solution contains 0.65 wt % of the SIBS copolymer and 0.10 wt % of a random copolymer of styrene and maleic anhydride containing approximately 14 wt % maleic anhydride (SMA14). The SMA14 copolymer is purchased from Sigma-Aldrich, or is available from Nova Chemical as Dylark 332.

Another control solution is prepared by mixing 0.75 wt % of the homopolymer poly(butyl methacrylate) (BMA) with the solvents and paclitaxel. BMA may be purchased from Sigma-Aldrich at a molecular weight of 337,000.

A second test solution containing 0.65 wt % of the BMA homopolymer and 0.10 wt % of SMA14 copolymer in prepared.

A third control solution is prepared with 0.75 wt % of a polystyrene-b-poly(ethylene-r-butylene)-b-polystyrene block copolymer (SEBS). The SEBS copolymer is obtained from Sigma-Aldrich, but is also known by the trade name Kraton™.

A third test solution is prepared using 0.65 wt % of the SEBS copolymer and 0.10 wt % of the SMA14 copolymer.

All solutions are prepared by (1) mixing the paclitaxel and tetrahydrofuran, (2) adding the copolymer or copolymers, (3) adding the toluene, (4) thoroughly mixing (e.g., overnight), and (5) filtering.

The solution is then placed in a syringe pump and fed to a spray nozzle. A stent is mounted onto a holding device parallel to the nozzle and, if desired, rotated to ensure uniform coverage. Depending on the spray equipment used, either the component or spray nozzle can be moved while spraying such that the nozzle moves along the component while spraying for one or more passes. After a carrier coating is formed in this fashion, the stent is dried, for example, by placing it in a preheated oven for 30 minutes at 65° C., followed by 3 hours at 70° C.

Three stents are formed in this manner for each of the various polymeric solutions.

Paclitaxel release is then measured as a function of time in PBS with 0.5 wt % Tween® 20 (polyoxyethylene(20) sorbitan monolaurate) available from Sigma-Aldrich. The results, presented as the cumulative release of paclitaxel as a function of time, are graphically illustrated in FIG. 1.

These results indicate that the release rate of a therapeutic agent from various polymeric carrier layers can be modulated by the addition of random copolymer containing styrene and maleic anhydride.

EXAMPLE 2

A series of solutions are prepared in a procedure similar to the procedure used in Example 1. All solutions contain the following: 25 wt % tetrahydrofuran (THF), 74 wt % toluene, 0.25 wt % paclitaxel and 0.75 wt % of a polymer composition or blend.

The control solutions are prepared by mixing 0.75 wt % the SIBS copolymer (see Example 1) or 0.75 wt % of the SMA14 copolymer (see Example 1) with the solvents and paclitaxel.

Test solutions are made containing the following polymeric constituents: (a) 0.5 wt % SMA14 and 0.25 wt % SIBS, (b) 0.3 wt % SMA14 and 0.45 wt % SIBS, (c) 0.2 wt % SMA14 and 0.55 wt % SIBS, (d) 0.1 wt % SMA14 and 0.55 wt % SIBS, (e) 0.15 wt % SMA14 and 0.60 wt % SIBS, (f) 0.1 wt % SMA14 and 0.65 wt % SIBS (two data sets), and (g) 0.05 wt % SMA14 and 0.7 wt % SIBS.

Figure 2A:
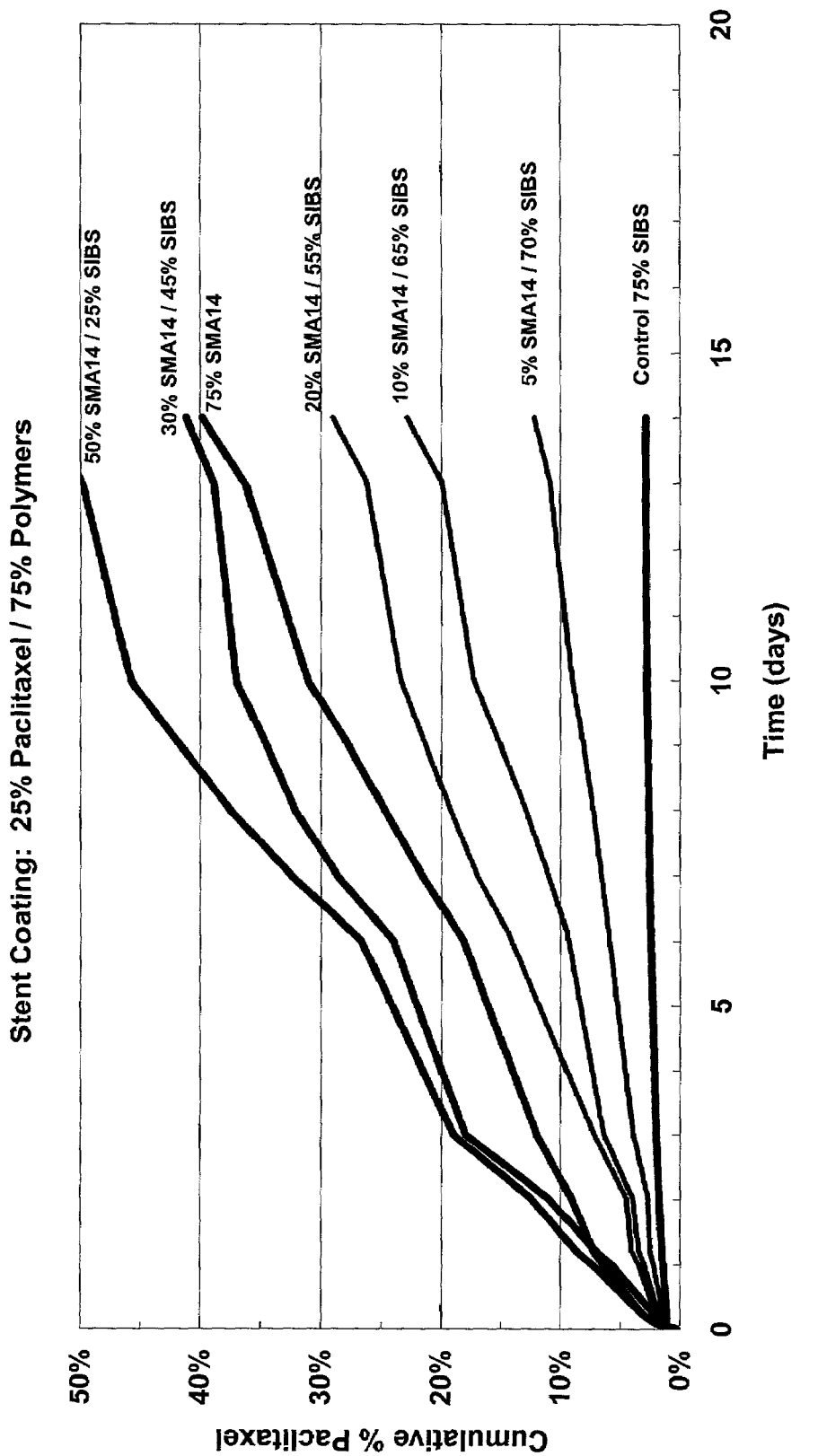
FIGS. 2A and 2B illustrate cumulative release of paclitaxel as a function of time for carrier layers containing paclitaxel and (a) a polystyrene-polyisobutylene-polystyrene block copolymer, (b) a random copolymer of styrene and maleic anhydride and (c) a polystyrene-polyisobutylene-polystyrene block copolymer blended with various amounts of a random copolymer of styrene and maleic anhydride, in accordance with an embodiment of the present invention.
Figure 2B:
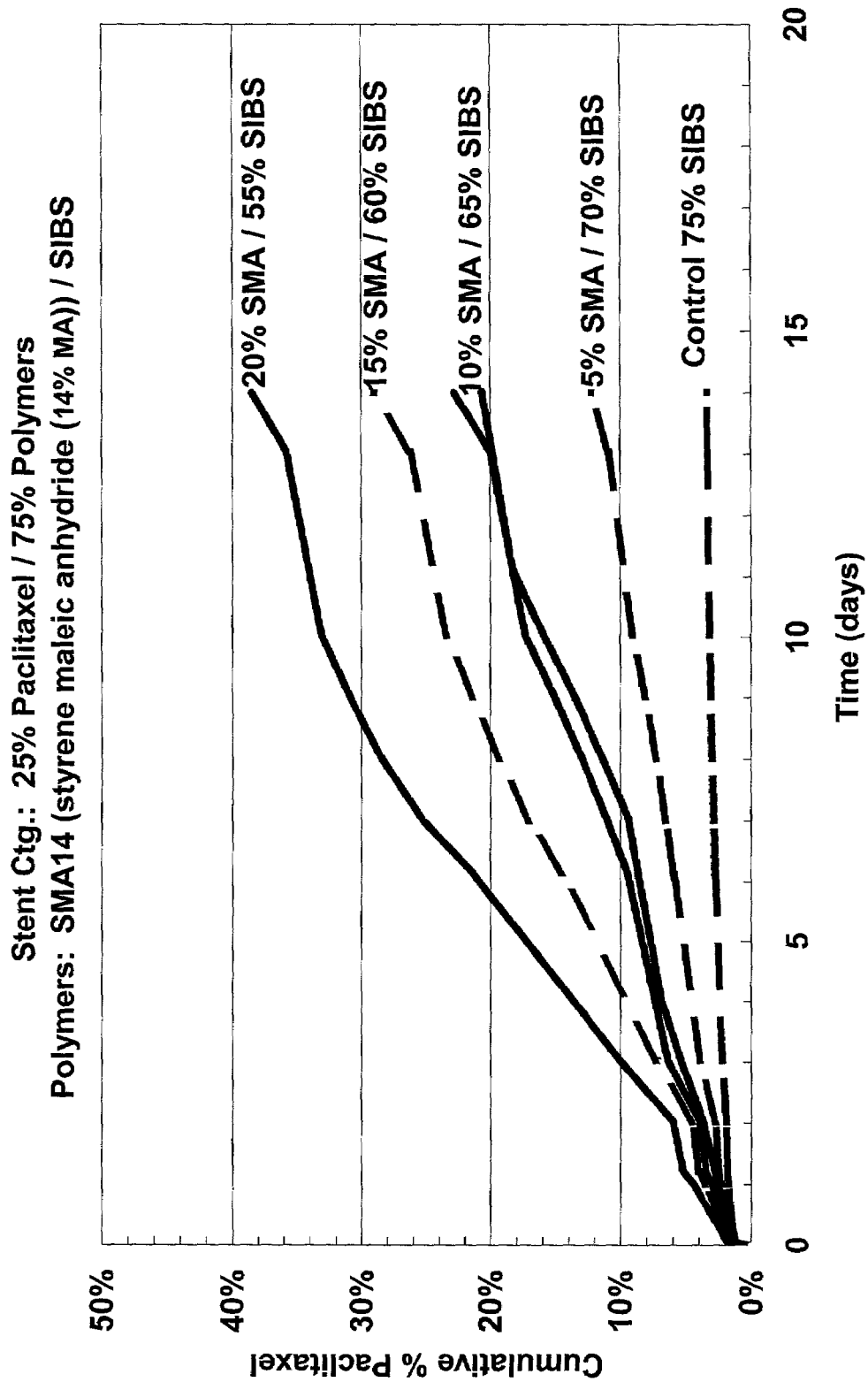

The solutions are applied to stents and dried according to the procedures of Example 1. Three stents are coated using each of the above solutions. The cumulative release of paclitaxel as a function of time is then measured as in Example 1. The results are graphically illustrated in FIGS. 2A and 2B.

These results indicate that the release rate of a therapeutic agent from a carrier layer comprising a polymeric carrier can be modulated by the addition of a random copolymer containing styrene and maleic anhydride in various proportions.

EXAMPLE 3

A series of solutions are prepared in a procedure similar to the procedure used in Example 1. All solutions contain the following: 25 wt % tetrahydrofuran (THF), 74 wt % toluene, 0.25 wt % paclitaxel and 0.75 wt % of a polymer or blend.

The control solution (two data sets) is prepared by mixing 0.75 wt % of the SIBS copolymer (see Example 1) with the solvents and paclitaxel.

Test solutions are made containing the following polymeric constituents: (a) 0.3 wt % styrene-co-acrylonitrile random copolymer containing approximately 25 wt % acrylonitrile (SAN25) and 0.45 wt % SIBS, (b) 0.10 wt % SAN25 and 0.65 wt % SIBS. SAN25 may be purchased from Sigma-Aldrich at a molecular weight of 165,000.

The solutions are applied to stents and dried according to the procedures of Example 1. Three stents are coated using each of the above solutions. The cumulative release of paclitaxel as a function of time is then measured as in Example 1. The results are graphically illustrated in FIG. 3.

These results indicate that the release rate of a therapeutic agent from a carrier layer comprising a polymeric carrier can be modulated by the addition of a copolymer of styrene and acrylonitrile in various proportions.

EXAMPLE 4

A series of solutions are prepared in a procedure like that used in Example 1. All solutions contain the following: 25 wt % tetrahydrofuran (THF), 74 wt % toluene, 0.25 wt % paclitaxel and 0.75 wt % polymer.

A control solution is prepared using 0.75 wt % of the SIBS copolymer (see Example 1).

A first test solution is prepared using 0.1% SMA14, a random copolymer of styrene and maleic anhydride containing approx. 14 wt % maleic anhydride (see Example 1) and 0.65% SIBS.

A second test solution is prepared using 0.722 wt % SIBS copolymer and 0.028 wt % of an alternating copolymer of styrene and maleic anhydride (SMA50) having a molecular weight of approximately 50,000, purchased from Scientific Polymer Products, Inc.

A third test solution is prepared using 0.722 wt % SIBS copolymer and 0.028 wt % of an alternating copolymer of styrene and maleic anhydride (SMA50) having a molecular weight of approximately 1700, also purchased from Scientific Polymer Products, Inc.

Note that the maleic anhydride (MA) content is the same for all test solutions.

SMA14:14% MA×10% SMA=1.4% MA total

SMA50:50% MA×2.8% SMA=1.4% MA total

Figure 4:
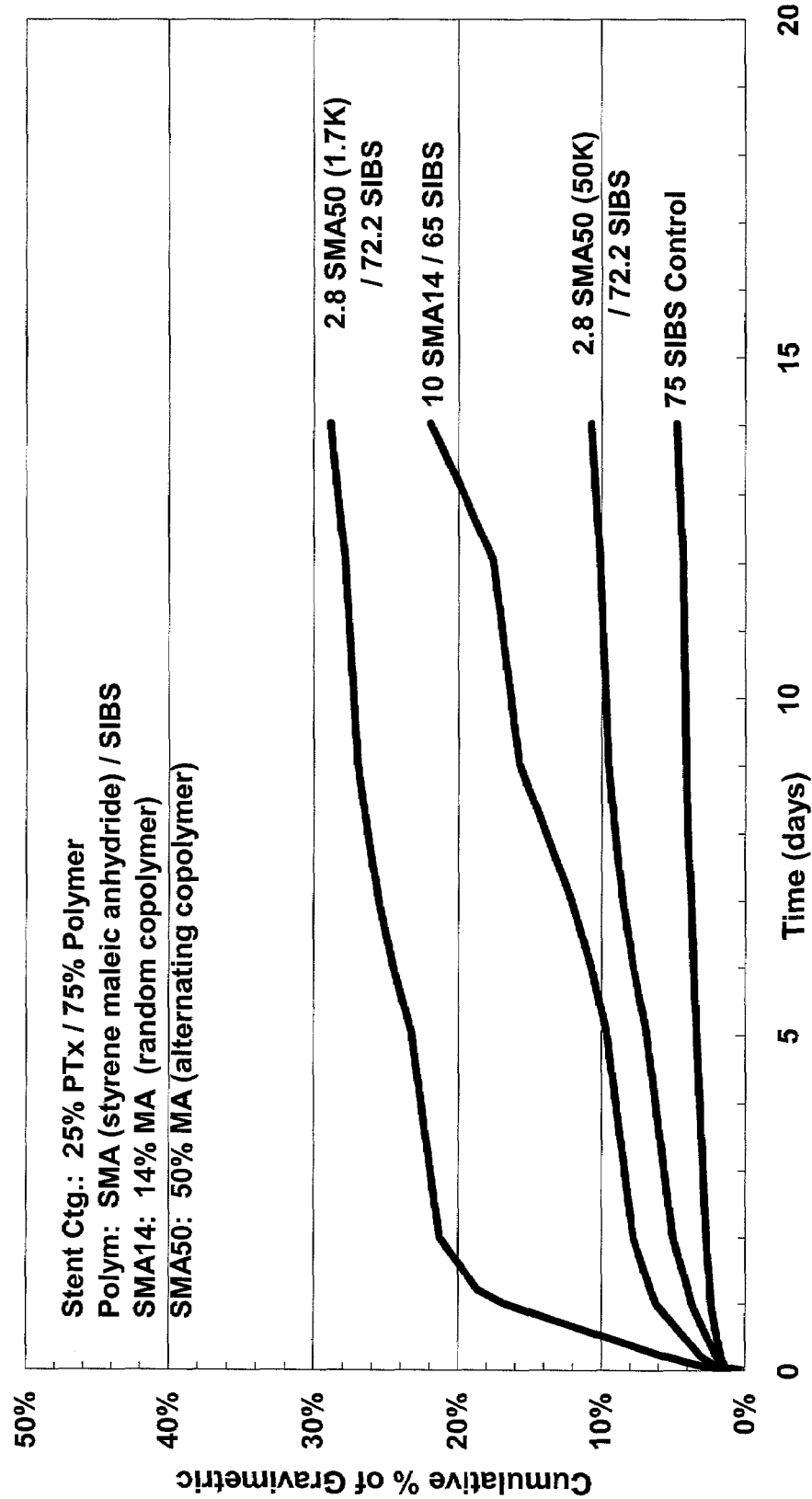
FIG. 4 illustrates cumulative release of paclitaxel as a function of time for carrier layers containing paclitaxel and (a) polystyrene-polyisobutylene-polystyrene block copolymer, (b) polystyrene-polyisobutylene-polystyrene block copolymer blended with a random copolymer of styrene and maleic anhydride, (c) polystyrene-polyisobutylene-polystyrene block copolymer blended with an alternating copolymer of styrene and maleic anhydride having a molecular weight of approximately 50,000, (d) polystyrene-polyisobutylene-polystyrene block copolymer blended with an alternating copolymer of styrene and maleic anhydride having a molecular weight of approximately 1700.

The solutions are applied to stents and dried according to the procedures of Example 1. Three stents are coated from each of the above solutions. The cumulative release of paclitaxel as a function of time is then measured as in Example 1. The results are graphically illustrated in FIG. 4.

These results indicate that the release rate of a therapeutic agent from a carrier layer comprising a copolymer of maleic anhydride and styrene can be modulated by varying the molecular weight of the copolymer in the carrier layer.

EXAMPLE 5

A series of solutions are prepared in a procedure like that used in Example 1. All solutions contain the following: 25 wt % tetrahydrofuran (THF), 74 wt % toluene, 0.25 wt % paclitaxel and 0.75 wt % polymer.

A control solution is prepared using 0.75 wt % of the SIBS copolymer (see Example 1).

A first test solution is prepared using 0.1% SMA14, a random copolymer of styrene and maleic anhydride containing approx 14 wt % maleic anhydride (see Example 1) and 0.65% SIBS.

A second test solution is prepared using 0.1 wt % SMA7, a random copolymer of styrene and maleic anhydride containing approximately 7 wt % maleic anhydride, and 0.65% SIBS.

Figure 5:
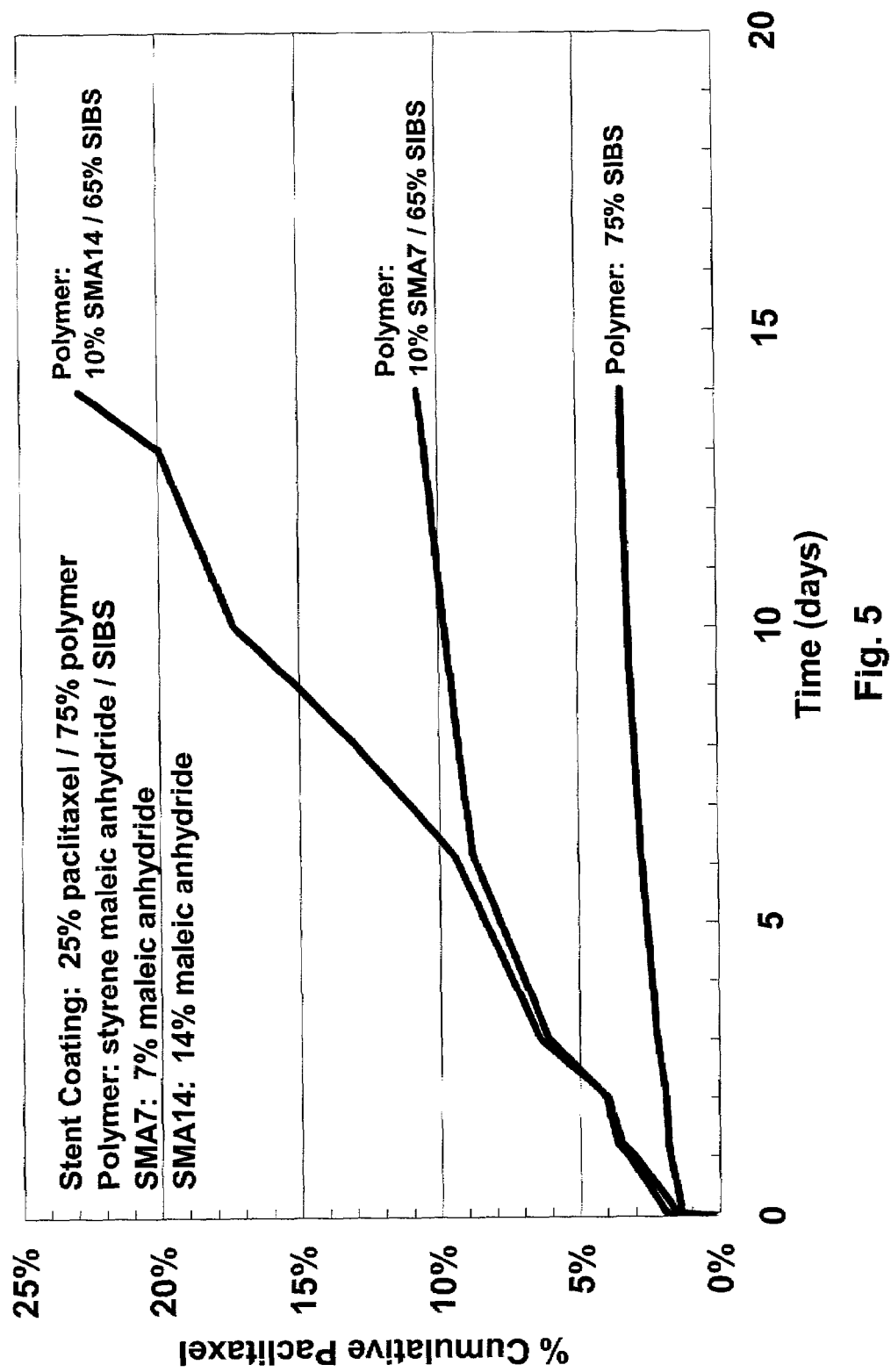
FIG. 5 illustrates cumulative release of paclitaxel as a function of time for carrier layers containing paclitaxel and (a) a polystyrene-polyisobutylene-polystyrene block copolymer, (b) a random copolymer of styrene and maleic anhydride containing approximately 7 wt % maleic anhydride blended with a polystyrene-polyisobutylene-polystyrene block copolymer, and (c) a random copolymer of styrene and maleic anhydride containing approximately 14 wt % maleic anhydride blended with a polystyrene-polyisobutylene-polystyrene block copolymer, in accordance with an embodiment of the present invention.

The solutions are applied to stents and dried according to the procedures of Example 1. Three stents are coated from each of the above solutions. The cumulative release of paclitaxel as a function of time is then measured as in Example 1. The results are graphically illustrated in FIG. 5.

These results indicate that the release rate of a therapeutic agent from a carrier layer containing a copolymer of maleic anhydride and styrene can be increased by varying the relative amounts of maleic anhydride monomer and styrene monomer in the copolymer.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A therapeutic-agent-releasing medical device comprising: (a) an implantable or insortable medical device; (b) a release layer disposed over at least a portion of the implantable or insertable medical device, said release layer comprising (i) a styrene copolymer selected from an alternating styrene copolymer and a random styrene copolymer and (ii) an additional polymer; and (c) a therapeutic agent selected from one or more of the group consisting of an anti-thrombotic agent, an anti-proliferative agent, an anti-inflammuatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms, said release layer regulating the rate of release of the therapeutic agent from the medical device such that said medical device exhibits a sustained release profile upon implantation or insertion of the device into a patient and said release layer being formed by a solvent-based technique in which said styrene copolymer and said additional polymer are dissolved or dispersed in a solvent which is applied to all or a portion of said implantable or insertable medical device, wherein less than 20% of the total release from the medical device occurs over the course of implanation/insertion in the body occurs within the first 1–3 days of administration.

2. The therapeutic-agent-releasing medical device of claim 1, wherein said release layer is a carrier layer that comprises said therapeutic agent.

3. The therapeutic-agent-releasing medical device of claim 1, wherein said release layer is a barrier layer disposed over a therapeutic-agent-containing region that comprises said therapeutic agent.

4. The therapeutic-agent-releasing medical device of claim 1, wherein said implantable or insertable medical device is selected from a catheter, a guide wire, a balloon, a filter, a stent, a stent graft, a vascular graft, a vascular patch, a shunt, and an intraluminal paving system.

5. The therapeutic-agent-releasing medical device of claim 1, wherein said implantable or insertable medical device is adapted for implantation or insertion into the coronary vasculature, peripheral vascular system, esophagus, trachea, colon, biliary tract, urinary tract, prostate or brain.

6. The therapeutic-agent-releasing medical device of claim 1, wherein said styrene copolymer is an alternating copolymer.

7. The therapeutic-agent-releasing medical device of claim 1, wherein said styrene copolymer is a random copolymer.

8. The therapeutic-agent-releasing medical device of claim 1, wherein said styrene copolymer is a random copolymer of styrene and maleic anhydride.

9. The therapeutic-agent-releasing medical device of claim 1, wherein said styrene copolymer is a random copolymer of styrene and acrylonitrile.

10. The therapeutic-agent-releasing medical device of claim 1, wherein said styrene copolymer is a copolymer comprising (a) a monomer comprising a carbon-carbon double bond and (b) a styrene monomer.

11. The therapeutic-agent-releasing medical device of claim 10, wherein said monomer comprising a carbon-carbon double bond is an alkylene monomer.

12. The therapeutic-agent-releasing medical device of claim 11, wherein said alkylene monomer is selected from ethylene, propylene, butadiene, butylene, isobutylene and isoprene.

13. The therapeutic-agent-releasing medical device of claim 10, wherein said monomer comprising a carbon-carbon double bond is a vinyl monomer.

14. The therapeutic-agent-releasing medical device of claim 13, wherein said vinyl monomer is selected from one or more of vinyl ethers, vinyl acetates, vinyl aliphatics, halogenated vinyl compounds, vinyl pyrrolidone, acrylonitrile, vinyl alcohols, and vinyl acrylamides.

15. The therapeutic-agent-releasing medical device of claim 10, wherein said monomer comprising a carbon-carbon double bond isan acrylic acid monomer or acrylic acid derivative.

16. The therapeutic-agent-releasing medical device of claim 15, wherein said acrylic acid monomer or derivative is selected from methyl acrylate, methyl methacrylate, acrylic acid, methacrylic acid, hydroxyethyl acrylate, hydroxyethyl methacrylate, glyceryl acrylate, glyceryl methacrylate, acrylamide, methacrylamide and ethacrylamide.

17. The therapeutic-agent-releasing medical device of claim 10, wherein said monomer comprising a carbon-carbon double bond is maleic anhydride or a maleic anhydride derivative.

18. The therapeutic-agent-releasing medical device of claim 1, wherein said additional polymer is an elastamer.

19. The therapeutic-agent-releasing medical device of claim 1, wherein said additional polymer is blended with said styrene copolymer in the release layer.

20. The therapeutic-agent-releasing medical device of claim 19, wherein the additional polymer is a copolymer comprising (a) one or more blocks of polyisobutylene and (b) one or more blocks of polystyrene or poly-alpha-methystyrene.

21. The therapeutic-agent-releasing medical device of claim 19, wherein the additional polymer is a copolymer comprising (a) one or more blocks of polystyrene and (b) one or more polymer blocks of ethylene and butylene.

22. The therapeutic-agent-releasing medical device of claim 19, wherein the additional polymer is a poly(butyl methacrylate).

23. The therapeutic-agent-releasing medical device of claim 1, wherein said additional polymer is crosslinked with said styrene copolymer in the release layer.

24. A method of forming the therapeutic-agent-releasing medical device of claim 1, comprising: (a) providing a solution comprising: one or more solvents, said styrene copolymer and said additional polymer; (b) applying said solution to a surface of said implantable or insertable medical device; and (c) removing said solvents from said solution to form said release layer.

25. The method of claim 24, wherein said solution further comprises said therapeutic agent.

26. The method of claim 24, wherein said solution is applied over a therapeutic-agent-containing region that comprises said therapeutic agent.

27. The method of claim 24, wherein said solution is applied by a solvent spraying technique.

28. A method of releasing a therapeutic agent within a patient comprising (a) providing the therapeutic-agent-releasing medical device of claim 1 and (b) implanting or inserting the therapeutic-agent-releasing medical device of into a patient.

29. The method of claim 28, wherein said medical device is selected from a catheter, a guide wire, a balloon, a filter, a stent, a stent graft, a vascular graft, a vascular patch, a shunt, and an intraluminal paving system.

30. The method of claim 28, wherein said medical device is inserted into the vasculature.

31. The method of claim 30, wherein said therapeutic agent is released in the treatment of restenosis.

32. A method of modulating a rate of release of a therapeutic agent by a release layer that (a) is disposed over at least a portion of an implantable or insertable medical device, and (b) comprises (i) a styrene copolymer selected from an alternating styrene copolymer and a random styrene copolymer and (ii) an additional polymer, said method comprising changing the composition of said release layer by a modification step selected from changing the amount of styrene copolymer relative to the amount of the additional polymer, changing the molecular weight of the styrene copolymer, changing the amount of the styrene monomer relative to the total amount of monomer within the styrene copolymer, and combinations thereof, wherein said release layer and (c) is formed by a solvent-based technique in which said styrene copolymer and said additional polymer are dissolved or dispersed in a solvent which is applied to all or a portion of said implantable or insertable medical device, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms, and wherein said medical device exhibits a sustained released profile after said modification step, and wherein said sustained release profile is a release profile in which less than 25% of the total release from the medical device that occurs over the course of implantation/insertion in the body occurs within the first 1–3 days of administration.

33. The method of claim 32, wherein the rate of release is modulated by changing the amount of styrene copolymer relative to the amount of the additional polymer.

34. The method of claim 33, wherein the rate of release of the therapeutic agent is increased by increasing the amount of the styrene copolymer relative to the amount of the additional polymer, or the rate of release of the therapeutic agent is decreased by decreasing the amount of the styrene copolymer relative to the amount of the additional polymer.

35. The method of claim 32, wherein the rate of release is modulated by changing the molecular weight of the styrene copolymer.

36. The method of claim 32, wherein the rate of release is modulated by changing the amount of the styrene monomer relative to the total amount of monomer within the styrene copolymer.

37. The therapeutic-agent-releasing medical device of claim 19, wherein the additional polymer is a copolymer comprising (a) one or more polyolefinic blocks and (b) one or polystyrenic blocks.

38. The therapeutic-agent-releasing medical device of claim 1, wherein said styrene copolymer is a copolymer comprising (a) a monomer selected from acrylonitrile, maleic anhydride, and a maleic anhydride derivative and (b) a styrene monomer, wherein said additional polymer is blended with said styrene copolymer in the release layer, and wherein said additional polymer is a copolymer comprising (a) one or more blocks selected from blocks of polyisobutylene and blocks of ethylene and butylene and (b) one or more blocks selected from blocks of polystyrene or blocks of poly-alpha-methylstyrene.

39. The therapeutic-agent-releasing medical device of claim 1, wherein said release solution is applied to all of said implantable or insertable medical device.

* * * * *

UNITED STATES PATENT AND TRADEMARK OFFICE
CERTIFICATE OF CORRECTION

PATENT NO. : 7,105,175 B2
APPLICATION NO. : 10/175334
DATED : September 12, 2006
INVENTOR(S) : Marlene C. Schwarz It is certified that error appears in the above-identified patent and that said Letters Patent is hereby corrected as shown below:

Col. 13, Line 11 through Line 12, before "application", change "solvent based" to -- solvent-based-- .

Col. 13, Line 28, end of line, change "solvent based" to -- solvent-based--.

Col. 14, Line 24, before "random", insert --a --.

Claim 17, Col. 17, Line 42, before "maleic", insert --a --.

Claim 28, Col. 18, Line 14, after "inserting" change "the therapeutic-agent-releasing medical device of into a patient.", to -- said therapeutic-agent-releasing medical device into a patient .-- .

Claim 37, Col. 19, Line 8, before "polystyrenic", insert --more --.

Claim 1, Col. 16, Line 20, before "medical", change "insortable" to -- insertable --.

Claim 1, Col. 16, Line 27 and 28, before "agent", change "anti-inflammuatory", to -- anti-inflammatory --.

Claim 1, Col. 16, Line 44, after "device", insert -- that --.

Claim 15, Col. 17, Line 31, change "isan", to -- is an --.

Claim 18, Col. 17, Line 45, last word in line, change "elastamer", to -- elastomer --.

Claim 32, Col. 18, Line 37, after "layer", delete "and (c)".

UNITED STATES PATENT AND TRADEMARK OFFICE
CERTIFICATE OF CORRECTION

PATENT NO. : 7,105,175 B2
APPLICATION NO. : 10/175334
DATED : September 12, 2006
INVENTOR(S) : Marlene C. Schwarz It is certified that error appears in the above-identified patent and that said Letters Patent is hereby corrected as shown below:

Claim 32, Col. 18, Line 51, before "profile", change "released" to -- release -- .

Signed and Sealed this

Thirteenth Day of March, 2007

JON W. DUDAS
*Director of the United States Patent and Trademark Office*